(12) United States Patent
Gunderson et al.

(10) Patent No.: US 12,330,129 B2
(45) Date of Patent: **\*Jun. 17, 2025**

(54) UTILIZATION OF PARTICLE SIZE MANIPULATION IN ADDITION TO PARTICLE AGGLOMERATION IN COMBINATIONS WITH MUTI PHOTON AND PHONON EMISSIONS ON OXIDIZING AGENTS CREATING AUGMENTED OXIDIZING AGENTS, AOAs

(71) Applicant: BIS SCIENCE LLC., Fort Worth, TX (US)

(72) Inventors: Marc W. Gunderson, Fort Worth, TX (US); Paul Dabney, Georgetown, TX (US)

(73) Assignee: BIS SCIENCE LLC., Fort Worth, TX (US)

( * ) Notice: Subject to any disclaimer, the term of this patent is extended or adjusted under 35 U.S.C. 154(b) by 425 days.

This patent is subject to a terminal disclaimer.

(21) Appl. No.: 17/889,690

(22) Filed: Aug. 17, 2022

(65) Prior Publication Data

US 2023/0090822 A1 Mar. 23, 2023

Related U.S. Application Data

(60) Provisional application No. 63/233,897, filed on Aug. 17, 2021.

(51) Int. Cl.
*B01J 19/12* (2006.01)
(52) U.S. Cl.
CPC ............ *B01J 19/12* (2013.01); *B01J 2219/12* (2013.01)

(58) Field of Classification Search
CPC .... A61L 2202/11; A61L 2202/14; A61L 2/22; A61L 2/26; B01J 19/123
See application file for complete search history.

(56) References Cited

U.S. PATENT DOCUMENTS

| 7,828,940 B2 | 11/2010 | Roseberry et al. |
| 9,963,017 B2 | 5/2018 | Kim et al. |

(Continued)

OTHER PUBLICATIONS

International Search Report and Written Opinion issued on Nov. 1, 2022, in connection with corresponding International Patent Application No. PCT/US2022/040570; 11 pages.

*Primary Examiner* — Sean E Conley
(74) *Attorney, Agent, or Firm* — David Staggs

(57) ABSTRACT

Methods, systems, and apparatuses for producing one or more of trioxygen, reactive nitrogen species, hydrogen and its ions, oxygen and its ions, and electronically modified oxygen derivatives from oxidizing agents that are exposed to certain frequencies of photon/phonon emissions, exposed for certain amounts of time, and exposed to certain intensities of photon/phonon emissions. The oxidizing agent or oxidizing agents can be exposed to multiple frequencies and wavelengths of photon/phonon emissions and multiple exposures of photon/phonon emissions. The methods displayed provide a new paradigm to perform photocatalytic oxidation of substrates using photon/phonon emissions and/ or MPA as energy input, trioxygen, hydrogen and oxygen and its isotopes as the catalysts and oxidizing agents as the oxygen source and the elimination or reduction of dissociation reactions to minimize hindrances to the reactions.

19 Claims, 2 Drawing Sheets

(56) References Cited

U.S. PATENT DOCUMENTS

| | | | |
|---|---|---|---|
| 11,654,413 B2* | 5/2023 | Gunderson | ............. C01B 13/10 422/29 |
| 2003/0209501 A1 | 11/2003 | Leung | |
| 2012/0186971 A1 | 7/2012 | Fink et al. | |
| 2019/0194041 A1 | 6/2019 | Lefebvre et al. | |
| 2020/0390920 A1 | 12/2020 | Dabney | |
| 2022/0249715 A1 | 8/2022 | Gunderson et al. | |

* cited by examiner

| Test Microorganism | Contact Time | Test Substance | Replicate | CFU/ml | Average CFU/ml | Average Percent Reduction Compared to Controls | Average Log₁₀ Reduction Compared to Controls |
|---|---|---|---|---|---|---|---|
| S. aureus ATCC 6538 | Pre-Treatment | Numbers Control | 1 | 3.32E+06 | 3.43E+06 | N/A | N/A |
| | | | 2 | 2.90E+06 | | | |
| | Post-Treatment | Numbers Control | 1 | 3.90E+06 | | | |
| | | | 2 | 3.60E+06 | | | |
| | 5 minutes | 1 PPM No photon emission | 1 | 4.10E+06 | 4.05E+06 | No Reduction | No Reduction |
| | | | 2 | 4.00E+06 | | | |
| | | 0.3% No photon emission | 1 | 4.10E+06 | 4.05E+06 | No Reduction | No Reduction |
| | | | 2 | 4.00E+06 | | | |
| | | 1 PPM Treated with photons | 1 | <1.00E+01 | <1.00E+01 | >99.9997% | >5.54 |
| | | | 2 | <1.00E+01 | | | |
| | | 0.3% Treated with photons | 1 | <1.00E+01 | <1.00E+01 | >99.9997% | >5.54 |
| | | | 2 | <1.00E+01 | | | |

Fig. 1 ated $E = K_l + P_l + K_s(\omega > \omega_F) + P_s(\omega > \omega_F) + K_d + P_d$ \quad (1)

UTILIZATION OF PARTICLE SIZE MANIPULATION IN ADDITION TO PARTICLE AGGLOMERATION IN COMBINATIONS WITH MUTI PHOTON AND PHONON EMISSIONS ON OXIDIZING AGENTS CREATING AUGMENTED OXIDIZING AGENTS, AOAs

BACKGROUND

The photon is a type of elementary particle. It is the quantum of the electromagnetic field including electromagnetic radiation such as light and radio waves, and the force carrier for electromagnetic force. A photon is the smallest discrete amount or quantum of electromagnetic radiation. It is the basic unit of all light. Photons are massless, so they always move at the speed of light in vacuum, 299792458 m/s (or about 186,282 mi/s). Like all elementary particles, photons are currently best explained by quantum mechanics and exhibit wave-particle duality, their behavior featuring properties of both waves and particles. Biophotons are photons of light in the ultraviolet and low visible light range that are produced or utilized by a biological system. They are non-thermal in origin, and the emission of biophotons is technically a type of bioluminescence, though bioluminescence is generally reserved for higher luminance luciferin/luciferase systems. When a photon gets to a material, it is absorbed by the material. The material then sets up an internal electromagnetic vibration that isn't precisely a "photon" (it's called a phonon to be specific). The phonon has a less-than-light velocity that depends on the properties of the material. A phonon is a definite discrete unit or quantum of vibrational mechanical energy, just as a photon is a quantum of electromagnetic or light energy. At each frequency, quantum mechanics principles dictate that the vibrational energy must be a multiple of a basic amount of energy, called a quantum, that is proportional to the frequency. Physicists call these basic levels of energy phonons. In a sense, then, "phonon" is just a fancy word for a particle of heat.

There are two types of atomic motion in a liquid: phonon motion and the diffusional motion due to an atom jumping between two equilibrium positions. In turn, the phonon and diffusional motion consists of kinetic and potential parts, giving the liquid energy as $$E = K_l + P_l + K_s(\omega > \omega_F) + P_s(\omega > \omega_F) + K_d + P_d \quad (1)$$

where Kl and Pl are kinetic and potential components of the longitudinal phonon energy, $K_s(\omega > \omega_F)$ and $P_s(\omega > \omega_F)$ are kinetic and potential components of the energy of shear phonons with frequency $\omega > \omega_F$ and Kd and Pd are kinetic and potential energy of diffusing atoms. Diffusion is the net movement of anything (for example, atoms, ions, molecules, energy) from a region of higher concentration to a region of lower concentration. Diffusion is driven by a gradient in concentration. So, phonon motion (heat motion) and diffusion motion work together so that temperature and composition are the same throughout a liquid.

Some particles of a different temperature are dissolved in a glass of water. At first, the particles are all near one top corner of the glass. If the particles randomly move around ("diffuse") in the water, they eventually become distributed randomly and uniformly from an area of high concentration to an area of low concentration, and organized (diffusion continues, but with no net flux). Likewise, the temperature also equalizes between the particles and the liquid as a function of the phonon's activity.

In practice, most materials are filled with an ever-changing mix of phonons that have different frequencies and are traveling in different directions, all superimposed on each other, in the same way that the seemingly chaotic movements of a choppy sea can (theoretically) be untangled to reveal a variety of superimposed waveforms of different frequencies and directions. But unlike photons (the particles that carry light or other electromagnetic radiation), which generally don't interact at all if they have different wavelengths, phonons of different wavelengths can interact and mix when they bump into each other, producing a different wavelength. This makes their behavior much more chaotic and thus difficult to predict and control.

Photoexcitation is the production of an excited state of a quantum system by photon absorption. The excited state originates from the interaction between a photon and/or phonon and the quantum system. On the atomic and molecular scale photoexcitation is the photoelectrochemical process of electron excitation by photon absorption when the energy of the photon is too low to cause photoionization.

Multi-photon absorption (MPA) or multi-photon excitation or non-linear absorption is the simultaneous absorption of two or more photons of identical or different frequencies in order to excite a molecule from one state (usually the ground state) to a higher energy, most commonly an excited electronic state. Multi-photon absorption is one of a variety of multi-photon processes. In this specific process, two or more photons are absorbed by a sample simultaneously. Neither photon is at resonance with the available energy states of the system, however, the combined frequency of the photons is at resonance with an energy state. In quantum mechanics, an excited state of a system is any quantum state of the system that has a higher energy than the ground state (that is, more energy than the absolute minimum). Absorption of two or more photons with different frequencies is called non-degenerate multi-photon absorption. Since multi photon absorption, MPA, depends on the simultaneous absorption of two or more photons, the probability of MPA is proportional to the square of the light intensity, thus it is a nonlinear optical process. The energy difference between the involved lower and upper states of the molecule is equal or smaller than the sum of the photon energies of the two or more photons absorbed. Multi-photon absorption is a third-order process, with absorption cross section typically several orders of magnitude smaller than one-photon absorption cross section.

SUMMARY

In one embodiment, a method for generating photo-oxidation products, photocatalytic products and/or photochemical combined with photocatalytic products which include one or more of reactive nitrogen species, hydrogen and its isotopes, oxygen and its isotopes, and electronically modified oxygen derivatives, reactive oxygen species, trioxygen, and free radicals, may be provided and may include applying at least one oxidizing agent to a target where the desired reaction is to take place; and before, and/or during, and/or after the at least one oxidizing agent is applied to the target where the desired reaction is to take place, applying photon/phonon and or MPA emission to the oxidizing agent and/or target where the desired reaction is to take place with a wavelength from 100 nm to 1200 nm which forms a synergistic reaction that produces the photo oxidation products, where the photo oxidation products include at least trioxygen and hydroxyl radical, also, wavelengths that photo-dissociate, trioxygen have been eliminated, or reduced or excluded from the photon/phonon emission.

In another embodiment, a system for performing the steps of the above method may be provided. The system can include a reaction area, in which the at least one oxidizing agent functions together with the photon and or phonon emission of certain wavelengths to lead to a synergistic reaction, so that the products of the reaction can be collected and separated any time during the reaction if desired, at least one oxidizing agent introducing component for applying the at least one oxidizing agent to the target where the desired reaction is to take place, and at least one photon and or phonon emitting component for creating the photon/phonon emission wherein wavelengths that can photo-dissociate, eliminate, or reduce trioxygen are excluded from the photon/phonon emission.

BRIEF DESCRIPTION OF THE DRAWINGS

The accompanying drawings illustrate various embodiments of systems, methods, and various other aspects of the embodiments. Any person with ordinary art skills will appreciate that the illustrated element boundaries (e.g., boxes, groups of boxes, or other shapes) in the figures represent an example of the boundaries. It may be understood that, in some examples, one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 1 provides exemplary test results.

DETAILED DESCRIPTION OF THE EMBODIMENTS

Figure 2:
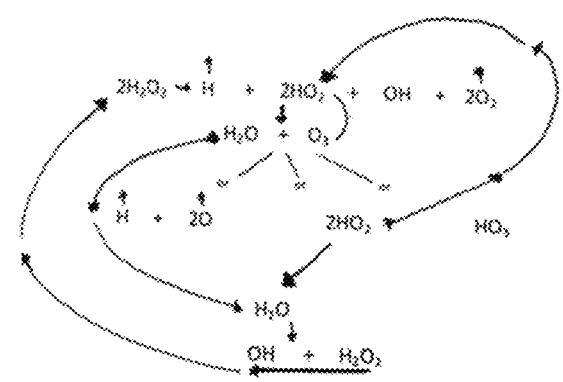
FIG. 2 is an exemplary diagram showing that a reaction can occur from a reactant molecule via an intermediate such as hydroperoxyl to form a trioxygen molecule, according to embodiments of the present disclosure.

Aspects of the present disclosure are disclosed in the following description and related drawings directed to specific embodiments. Alternate embodiments may be devised without departing from the spirit or the scope of the disclosure. Additionally, well-known elements of exemplary embodiments will not be described in detail or will be omitted so as not to obscure the relevant details of the disclosure.

As used herein, the word "exemplary" means "serving as an example, instance, or illustration." The embodiments described herein are not limiting, but rather are exemplary only. The described embodiments are not necessarily to be construed as preferred or advantageous over other embodiments. Moreover, the terms "embodiment or "embodiments" do not require that all embodiments of the disclosure include the discussed feature, advantage, or mode of operation.

Water absorbs UV radiation near 125 nm exiting the 3a1 orbit leading to dissociation into OH$^-$ and H$^+$. Through MPA this dissociation can be achieved by two or more photons at other nm wavelengths. This creates reactions and products that have been not previously reported or understood until the embodiments. Multi-photon absorption and Two photon absorption are the terms used to describe a process in which an atom or molecule makes a single transition between two of its allowed energy levels by absorbing the energy from more than a single photon.

Chemi-excitation via oxidative stress by reactive oxygen species, ROS, reactive nitrogen species, RNS, and/or catalysis by enzymes (i.e., peroxidase, lipoxygenase) is a common event in biomolecular systems. The embodiments herein can relate to utilizing photons and phonons in a synergistic chemi-excitation process that generates reactive oxygen species (ROS) and electronically modified oxygen derivatives (EMODs). This can also be called augmented oxidation agent (AOA). Such reactions can lead to the formation of triplet excited species such as trioxygen. This process is a contributing factor to spontaneous biophoton emission and has been indicated by studies demonstrating that biophoton emission can be increased by depleting assayed tissue of antioxidants or by addition of carbonyl derivatizing agents. Further support is provided by studies indicating that emission can be increased by addition of AOA electronically modified oxygen derivatives such as hydroxyl radicals, hydroperoxides, singlet oxygen, hydrogen, superoxide, and others. All electromagnetic radiation, radio waves through x-rays, moves in vacuum at a universal speed. This is the speed of light, c=30,000,000,000 centimeters per second (usually written in powers of ten, c=3×1010 cm/sec).

The constant value of the speed of light in vacuum goes against our intuition: it is expected that high energy (short wavelength) radiation would move faster than low energy (long wavelength) radiation. Light can be considered as a stream of minute packets of energy, photons and biophotons and generating phonons, which creates a pulsating electromagnetic disturbance. A single photon or biophoton differs from another photon or biophoton only by its energy. In empty space (vacuum), all photons and biophotons travel with the same speed or velocity. Photons and biophotons are slowed down generating phonons when they interact with different media such as water, glass or even air. This slowing down accounts for the refraction or bending of light. Refraction is the bending of a wave when it enters a medium where its speed is different. The refraction of light when it passes from a fast medium to a slow medium bends the light ray toward the normal to the boundary between the two media. The amount of bending depends on the indices of refraction of the two media and is described quantitatively by Snell's Law. As the speed of light is reduced in the slower medium, the wavelength is shortened proportionately. The energy of the photon and biophotons is not changed, but the wavelength is. This is discussed in more detail in the embodiments below when wavelengths of dissociation are described. Different energy photons and biophotons are slowed by different amounts in glass or water or other substances; this leads to the dispersion of electromagnetic radiation and phonons. Greater intensity of light means only that more photons were available to hit a target per second and more electrons could be ejected from a target, not that there was more energy per photon or biophoton.

The energy of the outgoing electrons depends on the frequency of photons used. There are two kinds of interactions through which photons deposit their energy; both are with electrons. In one type of interaction the photon loses all its energy; in the other, it loses a portion of its energy, and the remaining energy is scattered generating phonons. The energy (E) of the incoming photons and biophotons is directly proportional to the frequency which can be written as E=hf in which h is a constant. Max Planck first proposed this relationship between energy and frequency in 1900 as part of his study of the way in which heated solids emit radiation. In one example, the photoelectric (photon-electron) interaction, a photon transfers all its energy to an electron located in one of the atomic shells. The electron is ejected from the atom by this energy and begins to pass through the surrounding matter. The electron rapidly loses its energy and moves only a relatively short distance from its original location. The photon's energy is, therefore, deposited in the matter close to the site of the photoelectric interaction. The energy transfer is a two-step process. The photoelectric interaction in which the photon transfers its energy to the electron is the first step. The depositing of the energy in the surrounding matter by the electron is the second step. Phonons and electrons are the two main types of elementary particles or excitations generated with photon reactions.

If the binding energy is more than the energy of the photon, a photoelectric interaction cannot occur. This interaction is possible only when the photon has sufficient energy to overcome the binding energy and remove the electron from the atom or a MPA reaction can occur depositing more energy. The photon's energy is divided into two parts by the interaction. A portion of the energy is used to overcome the electron's binding energy and to remove it from the atom.

The remaining energy is transferred to the electron as kinetic energy (phonon) and is deposited near the interaction site. Since the interaction creates a vacancy in one of the electron shells, typically the K or L, an electron moves down to fill in. The drop in energy of the filling electron often produces a characteristic x-ray photon. The energy of the characteristic radiation depends on the binding energy of the electrons involved. Characteristic radiation initiated by an incoming photon is referred to as fluorescent radiation. Fluorescence, in general, is a process in which some of the energy of a photon is used to create a second photon of less energy. This process sometimes converts x-rays into light photons. Whether the fluorescent radiation is in the form of light or x-rays depends on the binding energy levels in the absorbing material.

In the embodiments, the linear attenuation coefficient ($\mu$) is the actual fraction of photons interacting per 1-unit thickness of material. Linear attenuation coefficient values indicate the rate at which photons interact as they move through material and are inversely related to the average distance photons travel before interacting. The rate at which photons interact (attenuation coefficient value) is determined by the energy of the individual photons or the MPAs and the atomic number and density of the material. This is important due to the activation of the augmented antimicrobial oxidizing agent, AOA, used in embodiments. In some embodiments, it is more desirable to express the attenuation rate in terms of the mass of the material encountered by the photons and or phonons rather than in terms of distance. The quantity that affects attenuation rate is not the total mass of an object but rather the area mass. Area mass is the amount of material behind a 1-unit surface area, and can be shown as, the area mass is the product of material thickness and density: Area Mass (g/cm2)=Thickness (cm)×Density (g/cm3).

The mass attenuation coefficient, using this formula, is the rate of photon and or phonon interactions per 1-unit (g/cm2) area mass. By establishing a linear attenuation coefficient that does not diminish too rapidly with the functioning distance so that sufficient numbers of photons and or phonons are available for enhancement of the oxidizing agent an effective augmented antimicrobial or augmented catalyzed, or augmented bleaching agent or augmented other effects of reactive oxygen species and oxidizing agent can be generated for use in the embodiments' process in plasma, liquid, gas. solid or a combination of these states of matter. It is also displayed in agglomeration process of the embodiments.

Brownian diffusion is the characteristic random wiggling motion of small particles, resulting from constant bombardment by surrounding molecules. Such irregular motions of pollen grains in water were first observed, and later similar phenomena were found for small smoke particles in air. In agglomeration, suspended particles tend to adhere one to the other creating bigger and heavier aggregates. The agglomeration process includes the transportation and collision of particles, and the attachment of the particles. Understanding particle agglomeration and aggregation and the mechanisms that cause such assemblies, such as diffusion, is important in a wide range of processes and applications.

Aggregation and agglomeration are two terms that are used to describe the assemblage of particles in a sample but clustering via agglomeration is irreversible. The main transport mechanisms by which particles can collide are Brownian motion, laminar or turbulent flow or relative particle settling and gravitational agglomeration. Gravitational agglomeration, which is dependent on the size of the particles and their terminal velocity, is one of the main focuses of this technology relating to the separation of particles in air, solutions or associated with a compound or material. Slowly settling particles interact with the more rapidly settling particles, leading to the formation of clusters. This process can be called agglomeration. Several different basic effects have been studied as being responsible for particle collision and agglomeration, which are mainly orthokinetic and hydrodynamic forces. In case of orthokinetic collisions the effective agglomeration rate constant or agglomeration input can be described as a product of the collision rate constant and an efficiency factor: $\beta=\psi(\varepsilon,\sigma)\beta coll$ $\beta coll$ increases linearly with the shear rate $\gamma$, that equals $\varepsilon/v$ in a turbulent stream, whereas the efficiency factor $\psi$ decreases strongly with $\gamma$ in this high shear region, and thus $\beta$ also decreases after having reached a maximal value at a rather low shear rate value. Although $\beta$ should be size-dependent, experimental agglomeration data can often be fitted with a size-independent input. It has been shown that $\beta coll$ has a dependence on the mean particle size. The efficiency factor includes the supersaturation dependence that is needed for the cementation of the particles. Brownian diffusion is instrumental in particle size selection for diffusion of photon/phonon enhanced oxidizing agent solutions dispersed in a fog, mist, vapor, spray, bolus, drop, stream or other methods of dispersion.

TABLE 1

| FOG CLASSIFICATION | DROPLET SIZE In microns | TIME FOR PARTICLE TO FALL 10 FEET (SECONDS) |
| --- | --- | --- |
| Wet Fog | 11-49 | 40-1,020 |
| Dry Fog | 6-10 | 1,019-12,000 |
| Extreme Dry Fog | 2-4 | 12,001-25,400 |
| Sub 2 Micron Dry Fog | <2 | >25,400 |

The relevance of droplet size is as follows. Rates of reaction are based on collision theory. Increasing the number of collisions can lead to faster reaction rate. Increasing the concentration causes more collisions so faster reaction rate. Temperature increases the speed of the particles so more collisions and faster rate. Size of particles has an effect on solubility reactions so smaller pieces or droplets have greater surface areas relative to the volume of the drop. A decrease in particle size causes an increase in the substance's total surface area when concentration remains unchanged.

Liquids evaporate only from the surface of the droplet. If the surface area of the droplet in relation to the volume of water is decreased, then the evaporation efficiency is increased. A substance existing in a liquid phase can be transferred to a gaseous phase by utilizing and controlling droplet size. This time needed for this phase transfer can be regulated by selecting the proper sized droplet.

The smaller the droplet size, the longer it can stay air borne. Therefore, the smaller the droplet size the faster and more efficient evaporation is achieved. The various micron droplets created by the system described in the embodiments evaporates at selected rates depending on application needs. If small size particles are selected, they can be sized so that they completely evaporate into the air before reaching most surfaces. This near 100% evaporation rate achieves near 100% chemical efficiency. A particle fall rate can be calculated based on density, size, and mass of the particle as well as the density of the air or gas it is placed in. Humidity also influences the fall rate outcome since at a low humidity a particle will tend to evaporate faster and lose size and mass as it remains air borne. These factors enable a selected size micron fog microbial suppression system and or agglomeration system and or bleaching system or other applicable system to utilize an extremely low volume and low concentration of a photon/phonon enhanced oxidizing agent solution.

This solution can then be deposited into a volume of liquid, plasma, air or gas or other suitable medium. This can be done through an existing HVAC system, a fogging device, a sprayer, a mister, an injector, a dropper, a spray can, an aerial spraying device, crop dusting or other suitable devices. This photon/phonon enhanced oxidizing agent system exhibits such a slow particle fall rate that when it is combined with the simultaneous phase change of these particles that a concentration of gas vapor (in this example of air borne dispersion) is created and maintained of the photon/phonon enhance oxidizing agent in the air. A progressive regression of colony forming units (CFUs) from the continuous presence of the photon/phonon enhanced microbial suppression system in this example provides a decontamination system consisting of the photon/phonon augmented oxidation agent, AOA, microbial suppression system solution and it affects substances that it contacts. Utilizing a photon/phonon and MPA augmented oxidation agent, AOA, microbial suppression system that includes particle size considerations for controlled dispersion and addresses agglomeration of inactivated microbes and other precipitates is a new multi-faceted technology described by this system. This combination provides a revolutionary new method for decontaminating areas, structures, food, liquids, animals, animal fluids, plants, buildings, pipelines, homes, offices, indoors and outdoors. A unique feature is that due to the low chemical concentrations made effective with the combination of the photon/phonon augmented oxidizing agent, AOA microbial suppression system is that there are no harmful effects on humans or animals or plants when administered at low concentrations so exposure to the agents can be on going and constant.

Another embodiment of the photon/phonon enhanced oxidizing agent system involves the dissociation of blood and other animal fluids. As an example, blood cells contain a dramatic amount of potentially usable components such as proteins, fats, minerals, elements and small molecular weight constituents that once separated allow disposal or repurposing of the resultant liquid in environmentally sound methods such as irrigation of crops. Animal fluids, blood, blood cells, microbes, and organic matter tend to be more difficult to dispose of as compared to serum or plasma. Blood, for example, tends to be less stable and contain total dissolved solids (TDS), total suspended solids (TSS), microbes and other components that complicate its disposal unless it is dissociated and separated. This is one of the major reasons why, for example, blood plasma (often simply referred to as plasma, i.e. an anticoagulated whole blood sample; deprived of cells and erythrocytes) and blood serum (often simply referred to as serum, i.e. coagulated whole blood; deprived of cells, erythrocytes and most proteins of the coagulation system, especially of fibrin/fibrinogen), are considered biohazards. Thus, an embodiment provides a decontamination system whereby blood components go through the described agglomeration process whereby photon and phonon augmented oxidizing agents, AOA are added to the blood causing dissociation of the blood into constituent components allowing for these components to be used for their water value and nutritional value and other desired purposes.

Organic matter pertains to any carbon-based compound that exists in nature. Living things are described as organic since they are composed of organic compounds. Examples of organic compounds are carbohydrates, lipids, proteins and nucleic acids. Since they are formed of carbon-based compounds, they are broken down into smaller, simpler compounds through decomposition and through dissociation when exposed to oxidizing agents that have been subject to photon and or phonon emissions from 100 nm through 1200 nm. Living organisms also excrete or secrete material that is considered an organic material. The organic matter from blood may contain useful substances that contribute a value when separated from the blood. This organic matter contains substances that can be repurposed as food sources, as fertilizer, as medicines or and other uses. Again, the decontaminated liquid that has had particles removed through agglomeration when exposed to oxidizing agents that have been exposed to photon and phonon emissions from 100 nm through 1200 nm with the wavelengths that dissociate trioxygen excluded or reduced can be used to irrigate land and/or for liquids for animals to ingest. The photon/phonon emissions can be a single wavelength or can exist as multiple wavelengths as long as the wavelengths that dissociate trioxygen are excluded. Reactions described in the embodiments provide a multitude of uses. In some uses, such as HVAC applications, a low concentration of 1 part per million (ppm) of an augmented oxidizing agent, AOA, or less may be used. In other examples of uses, a higher concentration of oxidizing agents of over 50% may be advantageous. Many variables such as temperature, opacity of reactants, pH and others influence the selection of concentration of oxidizing agents. An oxidizing agent can be added to a substance (target) for antimicrobial purposes. The effect of the phonon/phonon emissions may be desired to take place at a certain time or place. In this example, the photon/phonon emissions will not be applied to the oxidizing agent/target mixture until such time as the augmented reaction is desired to take place. In other instances, the photon/phonon emissions may be applied to the oxidizing agent before it is applied to the target. An example of this may be an antimicrobial and agglomeration effect in a HVAC system where applying the photon/phonon emissions to the oxidizing agent is better to suited to use than applying the photon/phonon emissions to the entire volume of ambient air of the HVAC system.

It is understood that appropriate separation/handling of animal fluids, blood, blood cells, microbes, and organic matter, e.g., by centrifugation, filtration, heating, cooling, precipitation, or analyte extraction is essential, before such processed sample can be properly and reliably disposed of or repurposed. As indicated above, serum or plasma may be obtained from whole blood and repurposed as nutrients or fertilizer, or disposed of as needed. Cells, cell constituents, microbes, organic matter, and erythrocytes may also be removed by filtration and/or centrifugation from blood or blood components or from other animal fluids but a lower cost method is desired over present commercially available techniques. In an embodiment of sample processing, the animal fluids, blood, blood cells, microbes and other organic matter of interest can first be separated from the majority of substances by dissociation, agglomeration and/or extraction methods when exposed to oxidizing agents that have been exposed to photon and phonon emissions from 100 nm through 1200 nm with the wavelengths that dissociate trioxygen excluded or reduced. Extraction can be performed in liquid phase or in a solid phase. Gross extraction of larger particles can be sequenced with extraction methods processing progressively smaller units until the desired resolution is obtained. To make this feasible, the embodiments allow for this process to be accomplished by photon/phonon emissions and their activation of oxidizing agent solutions.

In another embodiment, a photon/phonon emission augmented oxidizing agent, AOA, antimicrobial oxidizing agent solution can be applied to air via a HVAC system or other suitable means. A small micron (less than 20 microns) mist or fog photon/phonon MPA augmented oxidizing agent, AOA, microbial suppression system can be selected to utilize an extremely low volume and low concentration of a photon/phonon augmented oxidizing agent, AMA, antimicrobial oxidizing agent solution into a volume of air or gas.

This may be done through an existing HVAC system utilizing a electrostatic fog, fogging, misting, spraying, sprinkling, diffuser, atomizer or other suitable device. The application device may include an aerosolizing nozzle producing a small micron dry fog, An air compressor to push the solution through the nozzle at the desired rate, a metering pump to dispense the solution at a rate that will give the desired concentration in a building's ambient air, a control system to regulate and monitor the application of the solution. This small micron dry fog photon/phonon MPA augmented oxidizing agent, AOA, microbial suppression system exhibits such a slow particle fall rate that when it is combined with the simultaneous evaporation of these particles, a concentration of gas vapor is created and maintained of the photon/phonon activated antimicrobial agent in the air. A progressive regression of colony forming units (CFUs) from the continuous presence of the small micron dry fog microbial suppression system used in this example provides, in the ambient air, a decontamination system of air and surfaces that the small micron dry fog microbial suppression system solution contacts. As the photon/phonon augmented oxidizing agent, AOA, antimicrobial agent settles through the ambient air, it inactivates microbes, and any remaining hydrogen peroxide in the ambient air decomposes into oxygen and water. The small micron dry fog microbial suppression system may be designed so that most of the microbial inactivation occurs in the HVAC system ducts and in the higher levels of the buildings ambient air. By design, in this example, the concentration of hydrogen peroxide becomes lower as it is consumed inactivating microbes, by evaporation and by decomposition into oxygen and water. This demonstrates another, very different application of the technology displayed in the embodiments.

Exemplary FIG. 3 provides various test information and results.

Oxidative biocides such as chlorine and hydrogen peroxide ($H2O2$) remove electrons from susceptible chemical groups, oxidizing them, and become themselves reduced in the process. Oxidizing agents are usually low-molecular-weight compounds and are considered to pass easily through cell walls/membranes, whereupon they are able to react with internal cellular components, leading to apoptotic and necrotic cell death. Although biochemical mechanisms of action may differ between oxidative biocides, the physiological actions are largely similar. Oxidative biocides have multiple targets within a cell as well as in almost every biomolecule; these include peroxidation and disruption of membrane layers, oxidation of oxygen scavengers and thiol groups, enzyme inhibition, oxidation of nucleosides, impaired energy production, disruption of protein synthesis and, ultimately, cell death.

The generated photon/phonon MPA augmented oxidizing agent, AOA, microbial suppression system also acts like a filter in that a microbial particle cannot pass through it without colliding with a photon and or phonon enhanced antimicrobial particle. When a microbe collides with a photon and or phonon augmented oxidizing agent, AOA, antimicrobial particle, agglomeration occurs. As agglomerized microbial particles bind together, their mass increases as a unit. Gravitational forces acting on the photon and or phonon agglomerized microbial particles increase its velocity of fall. The photon and or phonon agglomerized microbial particles continue to gather more microbial particles as it falls through the selected medium such liquids, air or a gas. An analogy would be a snowball rolling downhill continually increasing in size as it advances downhill. Since photon/phonon augmented oxidizing agent, AOA, antimicrobial particles contain an enhanced oxidizing agent, the microbe that contacts the photon and or phonon augmented oxidizing agent, AOA, becomes agglomerized as it comes in contact with the antimicrobial sanitizer/disinfectant, filter particles. These agglomerized particles can settle or be filtered to remove them from the solution, air, gas, liquid or plasma.

This phenomenon can be called agglomeration and solving microbial problems with a photon/phonon MPA and AOA microbial suppression particle utilizes the theory of agglomeration mentioned previously in the embodiments. Agglomeration can be defined as the gathering of particle mass into a larger mass, or cluster. While this is occurring the photon/phonon AOA antimicrobial agent is killing and/or deactivating microbes. The agglomerated dead and/or deactivated microbe is pulled by gravitational forces and eventually settles from the substance being treated. The substance could be a liquid, gas, plasma or any suitable substance selected to be treated. This agglomeration of dead or inactivated microbes and other substances such as proteins and minerals is unique for a variety of reasons. As an example, in conditioned air, it has been shown that that even in common air filters, such as HEPA filters designed to filter out microorganisms, arrested microorganisms can grow and, in some cases, "grow through" the filter medium and seed the air with an ever increasing dose of microbes. Some organic media such as cellulose media provide nutrition for microbiological growth.

Another approach to decontamination in the embodiments provides for a progressive reduction the microbial count as the result of the application of a photon/phonon MPA AOA antimicrobial solution. This is accomplished by utilizing an antimicrobial oxidizing agent solution that has been augmented with photons and phonons to increase its effectiveness. The wavelength of the photons and or phonons can be from 100 nm to 1200 nm.

A unique aspect of this is the wavelengths that dissociate trioxygen have been purposely excluded from the photons and or phonons before transmission to the target where the desired interaction is to take place with the oxidizing agent. Trioxygen, oxygen and hydrogen are generated when the oxidizing agent is exposed to the photons and or phonons and creates a self-sustaining circuit of reactions that generates AOA electronically modified oxygen derivatives as long as conditions allow. This example utilizes hydrogen peroxide as a liquid and ambient air as a gas. This example illustrates that the described reaction may take place with reactants in different states of matter.

An example of this progressive reduction of the microbial count in ambient air is a room with 1,000,000 colony forming units (CFUs) is equipped with a system as described by the method of the embodiments. A small micron photon/pronon augmented oxidizing agent, AOA, antimicrobial dry fog having an augmented oxidizing agent that is continuously administered into the ambient air through an existing HVAC system at a concentration less than 1 part per million. This low concentration causes a reduction in the microbial CFUs as the small micron dry fog slowly settles through the ambient air killing CFUs at a rate of 20% (From the chart previously included a reader can see that our 1 ppm photon/pronon MPA augmented oxidizing agent antimicrobial solution actually achieved a 99.999% reduction in microbes but we are using 20% reduction in microbes in this example to make a point in the effect of the progressive reduction of microbes created with our system every 20 minutes creating gravitational agglomeration. After 20 minutes, the continuously administered small micron photon/phonon MPA AOA antimicrobial fog has reduced the 1,000,000 CFUs by 20% to 800,000 CFUs. As the progressive regression continues, the CFU count drops and after 1 hour of continuous treatment the CFU count is at 512,000. With continued progressive regression, there are 262,144 CFUs in the ambient air after 2 hours and 134,217 after 3 hours. The ambient air continues to get cleaner and cleaner and, after 5 hours, the progressive regression of the microbial count with this system of small micron photon and or phonon augmented oxidizing agent, AOA, antimicrobial dry fog consisting of a photon/pronon MPA AOA has reduced the CFU count to 35,184 CFUs. By continuing this reaction out for 8 hours, a reduction to 4772 CFUs is achieved, which is a 99.5% reduction in the microbial count in the ambient air over an 8 hour period utilizing a progressive regression of microbes achievable with the methods in the embodiments. Independent research lab testing shows little or no microbial reduction with 1 part per million of standard hydrogen peroxide with a 5 minute contact time. The same lab study shows over a 5 log reduction in microbial counts with the photon/phonon augmented oxidizing agent (hydrogen peroxide) solution described in the embodiments. The self-sustaining circuit of reactions where the wavelengths that dissociate trioxygen are excluded from the photon emission permits a reaction that has not previously been known.

Numerous applications across many industries have been found, from energy storage and production, medical, food, environmental and others, this method of combining, photocatalytic, photochemicallytic (photochemical and photocatalytic) and dissociation reactions with photon/phonon MPA emission augmented oxidizing agents opens a new frontier. This reaction was not previously known or utilized because conventional photocatalysis decomposes oxidizing agents by disproportionation and by promoting oxidizing agent reduction instead of hydrogen liberation. However, the embodiments herein provide a successful example of oxidizing agent and water dissociation. Trioxygen associates with the reactants and suppresses the reactant reduction, thus promoting hydrogen liberation. The organic photocatalytic system provides a basis of photocatalytic and photochemical and photocatalytic oxidizing agent and water dissociation.

An oxidizing agent is a chemical species that undergoes a chemical reaction in which it gains one or more electrons. Also, an oxidizing agent can be regarded as a chemical species that transfers electronegative atoms, usually oxygen, to a substrate.

The oxidizing agent can be called an oxygenation reagent or oxygen-atom transfer (OAT) agent. Oxidation reactions may involve oxygen atom transfer reactions and hydrogen atom abstraction which is a reaction where removal of an atom or group from a molecule by a radical occurs. The radiation commonly used in common antimicrobial, bleaching, and other chemical processes is known as UV-C. Ultra-Violet (UV) light is invisible to the human eye and is divided into UV-A, UV-B and UV-C. UV-C is found within 100-280 nm range. The germicidal action of UV-C is maximized at approximately 265 nm with reductions on either side. UV-C sources typically have their main emission at 254 nm. As a result, germicidal lamps can be effective in breaking down the DNA of microorganisms. This means that they cannot replicate and cause disease. UV radiation also can be used to eliminate trioxygen which is a reactive oxygen species (ROS). Reactive nitrogen species (RNS) is a subset of free oxygen radicals called reactive oxygen species (ROS). Trioxygen can also be used as a catalyst to convert H2O to products that exhibit health benefits, antimicrobial properties, bleaching properties, etching properties, and other products that and have wide commercial uses. In chemistry, photocatalysis is the acceleration of a photoreaction in the presence of a catalyst. Photocatalysts are materials that change the rate of a chemical reaction on exposure to light. In catalyzed photolysis, light is absorbed by a substrate. Photocatalytic activity (PCA) depends on the ability of the catalyst to create electron-hole pairs, which utilize electronically modified oxygen derivatives which are then able to undergo secondary reactions. Typically, two types of photocatalysis reactions are recognized, homogeneous photocatalysis and heterogeneous photocatalysis. Homogeneous photocatalysis: when both the photocatalyst and reactant are in the same phase, i.e. gas, solid, or liquid, such photocatalytic reactions are termed as homogeneous photocatalysis. Heterogeneous photocatalysis: when both the photocatalyst and reactant are in different phases, such photocatalytic reactions are classified as heterogeneous photocatalysis. When a photocatalyst is exposed to photon/phonon of the desired wavelength (sufficient energy), the energy of photons and or phonons is absorbed by an electron (e−) of valence band and it is excited to conduction band. In this process a hole (h+) is created in valence band. This process leads to the formation of photo-excitation state, and e− and h+ pair is generated. The hydroxyl radical is generated in both types of reaction. The difference in the two types of photocatalytic reactions are the forms and placements of the reactants and the photocatalysts.

An example of the described reaction used as a bleaching method can be illustrated with the preparation of wood pulp as used in paper manufacturing. One of the largest volume uses of hydrogen peroxide worldwide is in the paper industry. Hydrogen peroxide is used to increase the brightness of deinked pulp. The bleaching methods are similar for mechanical pulp in which the goal is to make the fibers brighter. By using the reaction described and enhancing the hydrogen peroxide with photons and or phonon with a wavelength of 100 to 1200 a synergistic reaction takes place generating ROS and EMODs and produces the photo-oxidation products and/or photocatalytic products and/or photochemical products by photon absorption of the oxidizing agent and target wherein the photo oxidation products and/or photocatalytic products and/or photochemical products created cause a greater bleaching result when the same concentration of oxidizing agent is used or allow for the same bleaching effect with a lower concentration. The self-sustaining circuit of reactions where the wavelengths that dissociate trioxygen are excluded from the photon emission permits a reaction that has not been described or utilized with a bleaching reaction previously.

Hydrogen peroxide is also used in the petroleum and petrochemical industries. An example is in the productions of plastics. Propylene oxide (PO), an important bulk chemical intermediate, is used for the manufacturing of polyurethanes (polyether polyols), polyesters (propylene glycol) and solvents (propylene glycol ethers). Hydrogen peroxide dissociates generating hydroxyl radicals that react with Propylene to propylene oxide. The methods described in the embodiments generate more hydroxyl radicals by exposing hydrogen peroxide to photon/phonon emissions of 100 nm-1200 nm with the wavelengths that dissociate trioxygen excluded. This enhanced hydrogen peroxide is more reactive in generating PO then un-enhanced (standard) hydrogen peroxide. The self-sustaining circuit of reactions where the wavelengths that dissociate trioxygen are excluded from the photon emission permits an enhanced reaction that has not been described or utilized with common reactions currently utilized in industries like the petroleum/petrochemical industries.

Hydrogen peroxide is used in the dairy industry and an antimicrobial preservative. By enhancing its effectiveness with the methods described in the embodiments, hydrogen peroxide exposed to photon/phonon emissions of 100 nm-1200 nm with the wavelengths that dissociate trioxygen excluded generates more hydroxyl radicals and other EMODs that exert a greater preservative and antimicrobial effect than un-enhanced $H_2O_2$.

Oxidizing agents are also used in the production of electronics such as microprocessors. By enhancing its effectiveness with the methods described in the embodiments, hydrogen peroxide and other oxidizing agents exposed to photon/phonon emissions of 100 nm-1200 nm with the wavelengths that dissociate trioxygen excluded generates more hydroxyl radicals and other EMODs. Such embodiments allow for a lower concentration of $H_2O_2$ to provide the required quantity of reactive oxygen species needed to etch circuit boards and other uses common in the electronics industry.

Listing all of the industries that utilize oxidizing agents and the reactive oxygen species/EMODs that they provide is not possible dues to the vast number of applications. Therefore, the applications and embodiments described herein are meant to provide examples, but not limit, the scope of the embodiments. In addition, a partial list of oxidizing agents includes, but is not limited to, Oxygen ($O_2$), trioxygen ($O_3$), Hydrogen (H), Hydrogen peroxide ($H_2O_2$) or other inorganic peroxides, Fenton's reagent, Fluorine ($F_2$), chlorine ($Cl_2$), or other halogens, Nitric acid ($HNO_3$) or nitrate compounds, Sulfuric acid ($H_2SO_4$), Peroxydisulfuric acid ($H_2S_2O_8$), Peroxymonosulfuric acid ($H_2SO_5$), or other Sulfur compounds, Hypochlorite, Chlorite, chlorate, perchlorate, or other analogous halogen compounds, chromic or dichromic acids, chromium trioxide, pyridinium chlorochromate (PCC), chromate, or dichromate compounds, or other hexavalent chromium compounds, potassium permanganate ($KMnO_4$), Sodium perborate, or other Permanganate compounds, Nitrous oxide ($N_2O$), Nitrogen dioxide/Dinitrogen tetroxide ($NO_2/N_2O_4$), urea, Potassium nitrate ($KNO_3$), Sodium bismuthate ($NaBiO_3$), ceric ammonium nitrate, ceric sulfate, or other Cerium (IV) compounds, peracetic acid, and Lead dioxide ($PbO_2$). This list is meant to serve as an example but is not inclusive of all oxidizing agents.

To monitor the synergistic reaction described in the embodiments, at least one or more sensors or other devices to indicate, detect, or inform of one or more of the following properties of the target or storage or environment: pH, temperature, salinity, density, trioxygen concentration, oxygen concentration, hydrogen concentration, oxidizing agent concentration, flow rate, microbial content, presence or absent of bacterial species, presence or absent of corrosive metabolites or otherwise corrosive substance, identification of a gas, presence or absent of an aqueous environment, presence or absent of high, low, or otherwise concentration of bacterial or non-bacterial, biomass or non-biomass, microbial content, or location of biofilms may be used. This list is not all inclusive, but instead is meant to provide examples of sensors and other devices that may be used singularly or in multiples. These sensors may be used to help regulate the described reaction. Temperature affects reaction rate as many of the described reactions are exothermic. A high pH favors hydroxyl radical formation at the expense of trioxygen formation. A low pH favors trioxygen formation over hydroxyl radical production. Flow rate may influence the effects of the described reaction by altering the amount of time substances are exposed to the photon and or phonons. Also, flow rate may be used to modulate exposure to variables such as temperature, flow rate, microbes, humidity and other conditions. This list is not inclusive but is meant as an example of effects of variables. Variables such as photon and or phonon emissions can affect the generation of ROS. These emissions can be less than 1 second in duration if the intensity of the emissions is high or the time of the applied emissions can be perpetual if the dose or intensity of the emissions is low. The temperature of the described reaction not only effects the reaction rate but also may be used to modulate enzymes present in the reactants. An example of this is the enzyme catalase. Catalase can hinder or stop reactions utilizing oxidizing agents by inactivating hydroxyl radicals. Catalase is inactivated by temperatures above certain limits. By using a sensor to measure temperature and by varying the temperature of the oxidizing agent and or the reactants enzymes such as catalase can have their effects modulated.

The photon/phonon generating apparatus used in the described method herein may be located in or adjacent to the oxidizing agent to be enhanced. In some instances, the photon/phonon generating apparatus may be located further from the oxidizing agent and methods of transmission of the photons and or phonons may be utilized. These methods of transmission may include fiber optics and other conductive media. Exposing oxidizing agents to photons from 100 nm and 1200 nm produces an AOA having unique EMODs that exhibits a residual effect demonstrated by its existence for hours, days, weeks and greater extended periods of time. The radiation wavelength of from 100 nm and 1200 nm may be produced from a variety of sources such as LEDs, lasers, natural light, electromagnetic radiation, arc lamps and other suitable sources. The list of radiation producing sources is not meant to limit sources to those listed but to serve as an example.

Processing of the target with an AOA containing EMODs in solution, which is a result of an oxidizing agent that has been exposed to radiation of certain wavelengths where the interaction of oxidizing agent and photons and phonons, when combined, produce a total effect that is greater than the sum of the effects of these individual components. The augmented oxidizing agent exhibits a pronounced residual effect. This residual effect is evidenced by the antimicrobial effect of the AOAs. The un-augmented oxidizing agents have been shown to exhibit an antimicrobial effect of approximately 30% at a dwell time of 5 minutes. The radiation of from 100 nm and 1200 nm has been shown to kill approximately 1% of the microbes that are exposed to it for 5 minutes. The augmented oxidizing agents demonstrate an antimicrobial effect over 100% greater than un-augmented oxidizing agents. This effect provides a concentration of an oxidizing agent with double the antimicrobial effect or a concentration of AOA can be utilized that is 50% or less of the concentration of the un-augmented oxidizing agent and exhibit the same antimicrobial activity. The oxidizing agent is exposed to radiation from 100 nm and 1200 nm. This creates an AOA that contains more EMODs than similar substances found in nature. These excess EMODs generate a newly discovered residual effect whereby the EMODs last for an extended period of time.

In a further embodiment, the effects of temperature and concentration may be described. A decrease in temperature would have the opposite effect when compared to an increase in temperature. With an increase in temperature (more phonons and phonons), there is an increase in the number of collisions between reactants. Increasing the concentration of a reactant increases the frequency of collisions between reactants and will, therefore, increase the reaction rate. An increase in temperature corresponds to an increase in the average kinetic energy of the particles in a reacting mixture—the particles move faster, colliding more frequently and with greater energy. Increasing concentration tends to increase the reaction rate too.

The rate, or speed, at which a reaction occurs depends on the frequency of successful collisions. A successful collision occurs when two reactants collide with enough energy and with the right orientation. That means if there is an increase in the number of collisions, an increase in the number of particles that have enough energy to react, and/or an increase in the number of particles with the correct orientation, the rate of reaction will increase.

The rate of reaction is related to terms of three factors: collision frequency, the collision energy, and the geometric orientation. Remember that the collision frequency is the number of collisions per second. The collision frequency is dependent, among other factors, on the temperature of the reaction.

When the temperature is increased, the average velocity of the particles is increased. The average kinetic energy of these particles is also increased. The result is that the particles will collide more frequently, because the particles move around faster and will encounter more reactant particles. However, this is only a minor part of the reason why the rate is increased. Just because the particles are colliding more frequently does not mean that the reaction will definitely occur.

The major effect of increasing the temperature is that more of the particles that collide will have the amount of energy needed to have an effective collision. In other words, more particles will have the necessary activation energy.

At room temperature, the hydrogen and oxygen in the atmosphere do not have sufficient energy to attain the activation energy needed to produce water:

$$O2(g)+H2(g)\rightarrow \text{No reaction}$$

At any one moment in the atmosphere, there are many collisions occurring between these two reactants. But what we find is that water is not formed from the oxygen and hydrogen molecules colliding in the atmosphere, because the activation energy barrier is just too high, and all the collisions are resulting in rebound. When we increase the temperature of the reactants or give them energy in some other way, the molecules have the necessary activation energy and are able to react to produce water:

$$O2(g)+H2(g)\rightarrow H2O(l)$$

There are times when the rate of a reaction may need to be slowed down. Lowering the temperature could also be used to decrease the number of collisions that would occur and lowering the temperature would also reduce the kinetic energy available for activation energy. If the particles have insufficient activation energy, the collisions will result in rebound rather than reaction. Using this idea, when the rate of a reaction needs to be lower, keeping the particles from having sufficient activation energy will keep the reaction at a lower rate. The humidity where the described reaction takes place effects the evaporation rate of the droplet if the desired location of the reaction is in the air. This variable, humidity, can change the rate of evaporation if the humidity is high and cause a decrease in the evaporation rate or cause an increase in the evaporation rate if the humidity is low in the area where the described reaction is to take place.

Where the described reaction takes place in a liquid or gaseous environment the opacity of the liquid or gas can affect the reaction rate. The more opaque a liquid or gas is, a higher dose of photons and or phonons may be utilized to achieve the desired reaction rate due to the opacities of the medium and its ability to affect the photon/phonon emissions. Likewise, the viscosity of the medium where the described reaction takes place can influence the reaction rate. A higher viscosity medium can retard the reaction rate due to the loss of photon/phonon energy as the photons and or phonons move through the medium. A lower viscosity medium causes the photons and or phonons to lose less energy as they move through the medium.

In some instances, the described reaction may have an increased reaction rate with the addition of a catalyst. Iron oxides catalyze the conversion of hydrogen peroxide (H2O2) into oxidants capable of transforming recalcitrant contaminants. This is an example of an additive effect of a catalyst.

In some instances, it may be desirable to slow down or halt the described reaction. Peroxidases or peroxide reductases are a group of enzymes which play a role in various chemical processes. They are named after the fact that they commonly break up peroxides.

Flocculants, also known as clarifying agents are used to remove suspended solids from liquids by inducing flocculation (the solids begin to aggregate forming flakes, which either precipitate to the bottom or float to the surface of the liquid, and then they can be removed or collected. Flocculants may be added to the described reaction before during or after the photon/phonon enhanced oxidizing agent is applied to the target where the described reaction is to take place. Flocculants may be added before the reaction to remove substances that are not desired to undergo the described reaction. In other instances, the flocculant may be added during the reaction or after the reaction depending on the desired outcome and use of the precipitated substance.

In one embodiment, a method for generating photo-oxidation products, photocatalytic products and/or photochemical combined with photocatalytic products which include one or more of reactive nitrogen species, hydrogen and its isotopes, oxygen and its isotopes, and electronically modified oxygen derivatives, reactive oxygen species, trioxygen, and free radicals, may be provided and may include applying at least one oxidizing agent to a target where the desired reaction is to take place; and before, and/or during, and/or after the at least one oxidizing agent is applied to the target where the desired reaction is to take place, applying photon/phonon and or MPA emission to the oxidizing agent and/or target where the desired reaction is to take place with a wavelength from 100 nm to 1200 nm which forms a synergistic reaction that produces the photo oxidation products, where the photo oxidation products include at least trioxygen and hydroxyl radical, also, wavelengths that photo-dissociate, trioxygen have been eliminated, or reduced or excluded from the photon/phonon emission.

In another embodiment, a system for performing the steps of the above method may be provided. The system can include a reaction area, in which the at least one oxidizing agent functions together with the photon and or phonon emission of certain wavelengths to lead to a synergistic reaction, so that the products of the reaction can be collected and separated any time during the reaction if desired, at least one oxidizing agent introducing component for applying the at least one oxidizing agent to the target where the desired reaction is to take place, and at least one photon and or phonon emitting component for creating the photon/phonon emission wherein wavelengths that can photo-dissociate, eliminate, or reduce trioxygen are excluded from the photon/phonon emission.

Exemplary FIG. 4 is an exemplary diagram showing that a reaction can occur from a reactant molecule via an intermediate such as hydroperoxyl to form a trioxygen molecule. FIG. 4 also shows an exemplary diagram showing a "stored" oxidizing effect that can be tapped to provide reactive oxygen species as needed, and the "stored" oxidizing effect feeds the self-sustained circuit of reactions so that reactive oxygen species are generated until one of the reactants is depleted. During its decay back to the ground state, the trioxygen molecule created in the described reaction emits energy. This released energy provides photons and/or phonons to help power the continuing self-sustaining circuit of reactions.

Radiation of 100 nm through 1200 nm emitted on water and hydrogen peroxide creates the reaction illustrated in the diagram below. Once the reaction is initiated, the reaction proceeds with or without further radiation exposure. The products such as trioxygen, hydrogen, oxygen and other generated electronically modified oxygen derivatives continue to "power" the reaction. An example of these products contributing to the continued reaction can be found in the decay of trioxygen. As it decays, photons and phonons are produced releasing energy to the reaction.

The below table displays research for the embodiments herein that illustrates the enhanced effectiveness produced by the above reaction. The control exhibited a 23.08% microbial reduction while the two samples of the radiation, photon/phonon augmented oxidizing agent, AMA, solution displayed a heightened effectiveness ranging between 76.92% and 84.62% microbial reduction at 4 weeks post exposure to augmenting radiation of 100 nm through 1200 nm. This heightened residual effect supports the claim of continuing self-sustaining circuit of reactions. This new art has not been described previously.

| | | | | | Week4 | |
|---|---|---|---|---|---|---|
| Test Microorganism | Contact Time | Test Substance | Replicate | CFU/ Carrier | Average Percent Reduction Compared to Controls | Average $Log_{10}$ Reduction Compared toControls |
| E. coli ATCC 11229 | Pre-Treatment | Numbers Control | 1 | 3.90E+04 | N/A | N/A |
| | 10 Minutes | Control Substance | 1 | 3.00E+04 | 23.08% | 0.11 |
| | | Sample 1 | 1 | 6.00E+03 | 84.62% | 0.81 |
| | | Sample 2a | 1 | 9.00E+03 | 76.92% | 0.64 |

By utilizing both types of PCA, a photon/phonon enhanced self-sustaining reaction is produced resulting in electronically modified oxygen derivatives that are continuously produced as long as reactants are present and the produced gases are not allowed to escape. Trioxygen is one of the potential photocatalysts. This results in an increased efficacy and a shelf life of increased and sustainable reactivity previously not producible with oxidizing agents. The pressure generated from the AOA reaction with the outgassing of trioxygen, hydrogen, oxygen and its ions and other created gases has been measured at approximately 47 psi in documented tests.

The embodiments further relate to producing one or more of reactive nitrogen species, trioxygen, hydrogen, and/or oxygen and/or its isotopes and/or electronically modifies oxygen derivatives, reactive oxygen species, free radicals, oxidizing molecules, oxygen-atom transfer (OAT) agents, oxidizing agents and/or various related species from oxidizing agents that are exposed to certain wavelengths of photon/phonon emission, exposed for certain amounts of time and exposed to certain intensities of photon/phonon emission. The oxidizing agents can be exposed to multiple frequencies of photon/phonon emission and multiple exposures of photon/phonon emission. The photons and or phonons can be supplied to the oxidizing agents continuously or in bursts or pulses. A continuous photon/phonon emission could be from a light emitting diode suspended in a container of an oxidizing agent emitting a constant dose of photons and or phonons. Bursts or pulses of photon/phonon emission could be utilized to rapidly enhance an oxidizing agent with 100 nm-1200 nm photon/phonon emissions from a high intensity laser where the high intensity bursts or pulses may be only seconds in duration, but these bursts or pulses could provide the same dose of photon/phonon emissions as a long duration continuous photon/phonon emission that was at a low dose. Dose is defined as intensity of the photon/phonon emission times the time of application. During research into the effects of photons and or phonons on oxidizing agents, a discovery was made that offers a revolutionary and multi-disciplinary advancement to science. The embodiments provide a new paradigm to perform photocatalytic oxidation of substrates using photon/phonon emission as energy input, generating photons and or phonons and producing trioxygen, oxygen and its ions and hydrogen as the catalysts and oxidizing agents as the oxygen source and dissociation reactions to minimize hindrances to the reactions. Understanding the chemistry of this new paradigm is essential for utilizing the reactivity. Photocatalytic activity (PCA) is commonly applied to a target where the desired reaction is to take place in two distinct ways. Further, the embodiments utilize both methods of applying photocatalytic activity to generate a unique reactions that continue even after the photon/phonon emissions that initiates the PCA is discontinued.

The associated research, which is reflected in the embodiments, explored PCA utilizing photon and or phonon emission and a significant discovery was made. It has been found that the destruction of trioxygen (O3) by certain wavelengths of photon/phonon emission prevents or retards reactions involved in the photocatalytic effects. The catalyst, trioxygen, was being eliminated by certain wavelengths of photon and or phonons that encourage dissociation reactions. By altering the production or availability of trioxygen, the reaction may include steps that allows and encourages or alternatively prevents or retards the generation of products such as oxygen and hydrogen, reactive nitrogen species, electronically modified oxygen derivatives and others. Some examples of EMODs are superoxide; hydrogen peroxide; hydroxyl radical; hydroxyl ion; and nitric oxide. These EMODs are generated by exposing Oxidizing Agents to radiation of a certain wavelength, generally between 100 nm and 1200 nm, where the interaction of these agents, oxidizing agents and radiation, when combined produce a total effect that is greater than the sum of the effects of the individual agents. This radiation exposure generates EMODs that last longer than typically found in nature by evidence of a residual effect which research, shown in the included table, has shown as an increased effect that lasts for days, thereby providing an AOA. The expected EMODs' life span when they are found naturally in nature is measured in nanoseconds. Exposing oxidizing agents to radiation produces an AOA having a unique EMOD that exhibits a residual effect demonstrated by its existence for hours, days, weeks and greater extended periods of time. The radiation wavelength of between 100 nm and 1200 nm may be produced from a variety of sources such as LEDs, lasers, natural light, electromagnetic radiation, arc lamps and other suitable sources. The list of radiation producing sources is not meant to limit sources to those listed but to serve as an example.

The below table shows actual testing results that illustrate the residual effect of Augmented Oxidizing Agents (AOAs) containing EMODs created by methods of the embodiments. The test substance was a solution of 3% hydrogen peroxide, which was exposed to radiation to form the AOA containing EMODs. The test substance or AOA was applied to target, which included a carrier with a viable bacteria concentration of anaerobic bacteria *Staphylococcus epidermidis* ATCC 12228. The AOA was applied 1 minute, 5 minutes, 10 minutes, 30 minutes, 1 hour, 12 hours, 24 hours, 2, days, 5 days, and 7 days after radiation exposure. After 7 days, AOA was again subjected to radiation for reactivation.

TABLE 3

| Test Microorganism | Contact time | Test Substance | Replicate | CFU/ML | Average CFU/ML | % reduction Compared to controls | LOG 10 Reduction compared to controls |
|---|---|---|---|---|---|---|---|
| S. aureus ATCC 6538 | 0 | Control | 1 | 3.32E+06 | 3.43E+06 | N/A | N/A |
| S. aureus ATCC 6538 | 0 | Control | 2 | 2.90E+06 | 3.43E+06 | N/A | N/A |
| S. aureus ATCC 6538 | 0 | Control | 1 | 3.90E_06 | 3.43E+06 | N/A | N/A |
| S. aureus ATCC 6538 | 0 | Control | 2 | 3.60E+06 | 3.43E+06 | N/A | N/A |
| S. aureus ATCC 6538 | 5 minutes | 1 ppm H2O2 no photon activation | 1 | 4.10E+06 | 4.05E+06 | No reduction | No reduction |
| S. aureus ATCC 6538 | 5 minutes | 1 ppm H2O2 no photon activation | 2 | 4.10E+06 | 4.05E+06 | No reduction | No reduction |
| S. aureus ATCC 6538 | 5 minutes | .3% H2O2 no photon activation | 1 | 4.10E+06 | 4.05E+06 | No reduction | No reduction |
| S. aureus ATCC 6538 | 5 minutes | .3% H2O2 no photon activation | 2 | 4.00E+06 | 4.05E+06 | No reduction | No reduction |
| S. aureus ATCC 6538 | 5 minutes | 1 ppm with photon activation | 1 | Less than 1.00E+01 | Less than 1.00E+01 | Greater than 99.997% | Greater than 5.54 |
| S. aureus ATCC 6538 | 5 minutes | 1 ppm with photon activation | 2 | Less than 1.00E+01 | Less than 1.00E+01 | Greater than 99.997% | Greater than 5.54 |
| S. aureus ATCC 6538 | 5 minutes | .3% with photon activation | 1 | Less than 1.00E+01 | Less than 1.00E+01 | Greater than 99.997% | Greater than 5.54 |

TABLE 3-continued

| Test Microorganism | Contact time | Test Substance | Replicate | CFU/ML | Average CFU/ML | % reduction Compared to controls | LOG 10 Reduction compared to controls |
|---|---|---|---|---|---|---|---|
| S. aureus ATCC 6538 | 5 minutes | .3% with photon activation | 2 | Less than 1.00E+01 | Less than 1.00E+01 | Greater than 99.997% | Greater than 5.54 |

There are statistical variations but when comparing the increased activation of the AOAs at 1 minute post augmentation with AQA that was augmented 7 days previously, the results are very similar. The AQA exhibits a pronounced residual effect. This residual effect is evidenced by the enhanced antimicrobial effect of the AOAs. The un-augmented oxidizing agents have been shown to exhibit an antimicrobial effect of approximately 30% at a dwell time of 5 minutes. The radiation of from 100 nm and 1200 nm has been shown to kill approximately 1% of the microbes that are exposed to it for 5 minutes. The Augmented Oxidizing Agents demonstrate an antimicrobial effect over 100% greater than un-augmented oxidizing agents. This effect provides a concentration of an oxidizing agent with double the antimicrobial effect or a concentration of AQA can be utilized that is 50% or less of the concentration of the un-augmented oxidizing agent and exhibit the same antimicrobial activity.

In one exemplary embodiment, it may be understood that after trioxygen is produced it will decay rapidly, because trioxygen is an unstable compound with a relatively short half-life. The half-life of trioxygen in liquid is shorter than in air. Trioxygen decays in liquids partly in reactions with hydroxyl radicals. The assessment of a trioxygen decay process always involves the reactions of two species: trioxygen and hydroxyl radicals. When these hydroxyl radicals are the dominant particles in the solution, it is called an advanced oxidation process (AOP).

The decay of trioxygen in contact with hydroxyl radicals is characterized by a fast initial decrease of trioxygen, followed by a second phase in which trioxygen decreases by first order kinetics. Dependent on the composition of the liquids, the half-life of trioxygen is in the range of seconds to hours in common testing. Factors influencing the decomposition of trioxygen in liquids are temperature, pH, ions, cations, environment and concentrations of dissolved matter and photon/phonon emissions. As mentioned above, trioxygen decomposes partly in hydroxyl radicals. When the pH value increases, the formation of hydroxyl radicals increases in a substance. In a solution with a high pH value, there are more hydroxide ions present, see formulas 0-1 and 0-2 below. These hydroxide ions act as an initiator for the decay of trioxygen:

$$O_3 + OH^- \rightarrow HO_2^- + O_2 \qquad \text{Equation 1}$$

$$O_3 + HO_2^- \rightarrow \cdot OH + O_2^{\cdot -} + O_2 \qquad \text{Equation 2}$$

The radicals that are produced during reaction 2 can introduce other reactions with trioxygen, causing more hydroxyl radicals to be formed. Dependent on the nature of dissolved matter in a liquid, these can accelerate or slow down the decay of trioxygen. Substances that accelerate this reaction are called promoters. Inhibitors are substances that slow down the reaction. When a liquid is infused with trioxygen, one often uses the term 'scavenging capacity' in reference to the decay rate of the trioxygen. Scavengers and inhibitors are entities that react with hydroxyl radicals and slow down the reaction between trioxygen and hydroxyl radicals. Some common methods of inhibiting the decay of trioxygen involve lowering the pH of the target liquid and using deionized solutions as dilutants when possible.

In further exemplary embodiments, oxidative reactions due to photocatalytic, homogenous effects may be described and utilized as follows:

The mechanism of hydroxyl radical production can follow paths such as:

$$O_3 + h\nu \rightarrow O_2 + O \qquad \text{Equation 3}$$

$$O + H_2O \rightarrow \cdot OH + \cdot OH \qquad \text{Equation 4}$$

$$O + H_2O \rightarrow H_2O_2 \qquad \text{Equation 5}$$

$$H_2O_2 + h\nu \rightarrow \cdot OH + \cdot OH \qquad \text{Equation 6}$$

Similarly, the Fenton system produces hydroxyl radicals by the following mechanism:

$$Fe^{2+} + H_2O_2 \rightarrow HO\cdot + Fe^{3+} + OH^- \qquad \text{Equation 7}$$

$$Fe^{3+} + H_2O_2 \rightarrow Fe^{2+} + HO\cdot_2 + H^+ \qquad \text{Equation 8}$$

$$Fe^{2+} + HO\cdot \rightarrow Fe^{3+} + OH^- \qquad \text{Equation 9}$$

In photo-Fenton type processes, additional sources of OH radicals should be considered: through photolysis of H2O2 and H2O, and through reduction of Fe3+ ions under photon/phonon excitation:

$$H_2O_2 + photons \rightarrow HO\cdot + HO\cdot \qquad \text{Equation 10}$$

$$Fe^{3+} + H_2O + photons \rightarrow Fe^{2+} + HO\cdot + H^+ \qquad \text{Equation 11}$$

Oxidative reactions due to photocatalytic heterogenous effect:

$$h^+ + H_2O \rightarrow H^+ + \cdot OH \qquad \text{Equation 12}$$

$$2h^+ + 2H_2O \rightarrow 2H^+ + H_2O_2 \qquad \text{Equation 13}$$

$$H_2O_2 \rightarrow 2\cdot OH \qquad \text{Equation 14}$$

The reaction of H2O2=H2O+O is typically referenced in most literature as the predominant disassociation reaction associated with hydrogen peroxide and results in the production of oxygen and water. There are a number of reaction pathways such as dissociation to hydronium ion and hydroperoxide, and disproportionation to dioxygen and water. Note that TRIOXYGEN is not produced in the above reactions.

Trioxygen is photo-dissociated by certain wavelengths of photon/phonon emissions. While trioxygen may be created, it may also be dissociated depending on the desired outcome of the reaction. The table below is a partial list of the products of trioxygen dissociation and a partial list of the wavelengths associated with those products:

| | |
|---|---|
| $O(^3P) + O_2(^3\Sigma)$ | 1118 nm-1119 nm |
| $O(^3P) + O_2(^1\Delta)$ | 599 nm-600 nm |
| $O(^3P) + O_2(^1\Sigma)$ | 452 nm-453 nm |
| $O(^1D) + O_2(^3\Sigma)$ | 402 nm-403 nm |
| $O(^1D) + O_2(^1\Delta)$ | 307 nm-308 nm |
| $O(^1D) + O_2(^1\Sigma)$ | 263 nm-264 nm |
| $O(^3P) + O(^3P) + O(^3P)$ | 197 nm-198 nm |

In one path, the embodiments describe one or more reactions whereby the trioxygen is not totally or partially photo-dissociated by photon/phonon emissions. Trioxygen then becomes a photocatalyst for newly discovered reactions. The resulting reaction is one that has not previously been described. Trioxygen is produced and retained when the above-mentioned wavelengths of photodissociation are excluded and the pH is favorable to trioxygen generation. This exclusion coupled with photocatalytic reactions generating one or more of reactive nitrogen species, trioxygen, hydrogen, and/or oxygen and/or its isotopes and/or electronically modifies oxygen derivatives, reactive oxygen species, free radicals, oxidizing molecules, oxidizing agents and/or various related species from oxidizing agents that are exposed to certain frequencies of photon/phonon emissions. The reaction with OH– is the initial decomposition step of trioxygen decay, the stability of a trioxygen solution is thus highly dependent on pH and decreases as alkalinity rises. At pH above 8 the initiation rate has, in the presence of radical scavengers, been shown to be proportional to the concentrations of trioxygen and OH–. However, in acidic solutions the reaction with OH– is not the initiation step. Predicted reaction rates below pH 4 including a mechanism based only on reaction with OH– are much lower than those determined experimentally. The trioxygen equilibrium reaction below becomes significant and the initiation reaction is catalyzed.

$$O_3 \underset{k_{-17}}{\overset{k_{17}}{\rightleftharpoons}} O + O_2$$

$$k_{17} = 10^{-7} \text{ s}^{-1}$$
$$k_{-17} = 4 \cdot 10^9 \text{ M}^{-1}\text{s}^{-1}$$

The atomic O continues to react with H2O, or forms an excited trioxygen radical, from recombination, that subsequently reacts with H2O, as shown in the two equations below, respectively.

$$O + H_2O \longrightarrow 2HO^\bullet$$

$$O_3^* + H_2O \longrightarrow H_2O_2 + O_2$$

The species formed can then react further, forming other radicals such as O2–/HO2. The propagating products, HO• and HO2, diffuse and react with trioxygen in the continuing self-sustaining circuit of reactions. Only low concentrations of the terminating species are present in the solution which is why the significant part of the termination reactions below also takes place.

$$HO^\bullet + HO^\bullet \underset{}{\overset{k_{20}}{\rightleftharpoons}} H_2O_2$$

$$k_{20} = 6 \cdot 10^9 \text{ M}^{-1}\text{s}^{-1}$$

-continued $$HO^\bullet + HO_2 \underset{}{\overset{k_{21}}{\rightleftharpoons}} H_2O + O_2$$

$$k_{21} = 7 \cdot 10^9 \text{ M}^{-1}\text{s}^{-1}$$

$$HO_2 + HO_2 \underset{}{\overset{k_{22}}{\rightleftharpoons}} H_2O_2 + O_2$$

$$k_{22} = 8 \cdot 10^5 \text{ M}^{-1}\text{s}^{-1}$$

An example of an oxidizing agent involved in this reaction; H2O2+photon/phonon emissions from 100 nm to 1200 nm (where the wavelengths causing photodissociation of trioxygen have been excluded), when H2O2 and this selective photon/phonon emission are combined, this reaction yields H2+2HO2 which in turn yields H2O+trioxygen. This self-sustaining circuit of reactions will continue as long as the correct wavelength of photons are present and H2O2 (oxidizing agent) is present. The 2 paths of this reaction can yield various products but particularly H2 and O2 or yield 2HO2. The trioxygen that is created on this path enters and exists in this self-sustaining circuit of reactions with H2O and the self-sustaining circuit of reactions will continue to function and is dependent on the supply of trioxygen or hydroperoxyls generated from reactions of trioxygen or hydroxyl radicals or generated from reactions of trioxygen with other reactants. A self-sustaining circuit of reactions includes numerous reactions and potential reactions that may vary depending on variables such as temperature, pH, catalysts, and others. The more basic and recognizable reaction is the self-sustaining circuit of reactions where it is trioxygen that reacts with water producing at various stages O2, hydroxyls, H2, HO3, HO4, and hydroperoxyls. Exposure of oxidizing agents such as hydrogen peroxide with the entire UV spectrum of radiation produces hydroxyl radicals but limited or no trioxygen due to the wavelengths that are present that also destroy trioxygen. This dissociation of trioxygen was previously undiscovered or unappreciated and, without this step, the products of this reaction could not be produced in a self-sustaining circuit of reactions. Furthermore, if this step is performed, but performed in the wrong sequence, the reaction will not have the desired results and the self-sustaining chain of reactions will not occur. Hydroxyl radicals are very reactive free radicals, but they only exist for extremely brief periods of time measured in nano seconds. This nano second long existence leads to a short-term effect whereby the hydroxyl radicals exert an influence that cannot be stored or held in reserve. While this immediate effect has many uses, the production of trioxygen by the photon/phonon emissions and interaction with oxidizing agents with photons and or phonons of certain wavelengths that exclude those wavelengths associated with the dissociation of trioxygen excluded, produces reactants such as hydroperoxyls that react to form trioxygen. With trioxygen in a self-sustaining circuit of reactions, a steady stream of products is created, one being a chain of hydroxyl radicals that can now exert a more long-lasting effect. This self-sustaining circuit of reactions also allows for a "shelf life" where the reaction can be maintained and stored for future use even after the photon/phonon exposure to the oxidizing agent has been terminated. An effect that can now be measured in minutes, hours, or days due to the continued effect of the reaction products created.

In reference to the discussed reactions, the embodiments explain new discoveries whereby the photon/phonon emissions directed at the oxidizing agent or oxidizing agents alters the typical reactions. This can be accomplished by excluding wavelengths of photon/phonon emissions that inhibit the formation of trioxygen or wavelengths that destroy trioxygen and by retaining the created gasses. This creates and allows trioxygen and the other created gasses to function as a catalyst.

The following embodiment relates to the working model of the equation for the self-sustaining circuit of reactions. In chemical kinetics, an equation dictates that a chemical reaction utilizing oxidizing agents proceeds via a decomposition reaction where an electron induced decomposition by photons and or phonons (excluding wavelengths inhibiting trioxygen formation or destroying trioxygen) of the oxidizing agent proceeds. X defines potential decomposition by-products such as reactive nitrogen species, hydroxyls, hydroperoxyls, electronically modified oxygen species, hydrogen and oxygen and others. A reaction can occur from a reactant molecule via an intermediate such as hydroperoxyl to form a trioxygen molecule, as shown below.

OXIDIZING AGENT+photon/phonon dose (excluding wavelengths that dissociate trioxygen (O3)) →O3+X.

In reference to the above reactions, this embodiment explains discoveries whereby the photon and or phonon emissions directed at the oxidizing agent alters the typical reaction. This can be accomplished by excluding wavelengths of photon and or phonon emissions that inhibit the formation of trioxygen or wavelengths that destroy trioxygen. Photochemical reactions are a chemical reaction initiated by the absorption of energy in the form of photons and phonons. The consequence of molecules' absorbing photons and phonons is the creation of transient excited states whose chemical and physical properties differ greatly from the original molecules. photochemical combined with photo-catalytic trioxygen generation (PTG) splits water molecules into H2, O2, and O3. PTG can achieve high dissolution in water without other competing gases found in the corona discharge method of trioxygen production, such as nitrogen gases present in ambient air. This method of generation can achieve consistent trioxygen concentration and is independent of air quality because water is used as the source material. Production of trioxygen photochemically was previously not utilized in reactions such as those described in the methods displayed because of the required photon/phonon wavelength exclusion required to produce trioxygen as compared to producing oxygen as the typical reaction product was not understood or underappreciated. However, as described herein, it is possible to change the production of oxygen by careful selection of photon wavelengths such that trioxygen is preferentially produced.

Previous research involving UV radiation utilized bulbs (devices emitting electromagnetic energy) that produced a bell-shaped curve of radiation that in this bell shaped curve produced wavelengths of dissociation of compounds and wavelengths creating the same compounds. While there may have been a greater influence of either the creation or dissociation wavelength, the resulting reaction was at best inefficient.

Thus, in the embodiments, to generate more trioxygen, photochemical combined with photocatalytic trioxygen generation (PTG), where wavelengths of photons/phonons that dissociate trioxygen are excluded and the dose of photon/phonon emission can be increased by increasing the intensity, the time the photon/phonon emission is applied and other variables to the dose where some or all variables may be changed to influence the result of the reaction. This data helps to demonstrate the nature of the initial complex which decomposes an oxidizing agent upon photon/phonon exposure. Further, multiple reaction sequences are possible. First, comparing the electronic structure of the water and the oxidizing agent molecules, the trioxygen should cleave at least one oxygen-hydrogen bond of the water molecule in the self-sustaining circuit of reactions, which, in turn, forms the hydroxyl radical plus atomic hydrogen. Two of the hydroxyl radicals can recombine in an exoergic reaction to form an oxidizing agent molecule. The reaction reversibility dictates that upon application of trioxygen to the water molecule, the latter can decompose in one step to form oxygen atoms plus molecular hydrogen. The oxygen atom in the presence of trioxygen can react now with a water molecule by an insertion into an oxygen-hydrogen bond to form hydrogen peroxide but with the continued application of trioxygen, the generation of H2O2 may be delayed or excluded. As the reaction is delayed, oxygen and hydrogen may be liberated in sufficient quantities to alter the quantity of available components thus preventing or minimizing the production of H2O2. Alternatively, the oxygen atom can add itself to the oxygen atom of the water molecule forming a short-lived intermediate which rearranges then via hydrogen migration to the hydrogen peroxide molecule. These equations display an electron induced decomposition of two water molecules in close proximity. [(H2O(X A1))2] to form a hydrogen peroxide molecule while liberating hydrogen and oxygen.

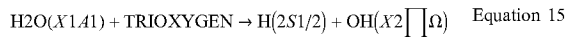 Equation 15

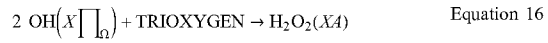 Equation 16

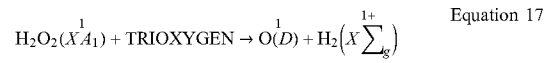 Equation 17

 Equation 18

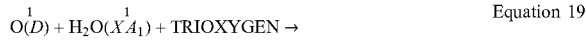 Equation 19

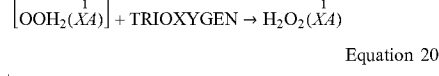

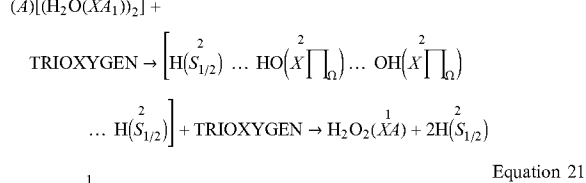 Equation 20

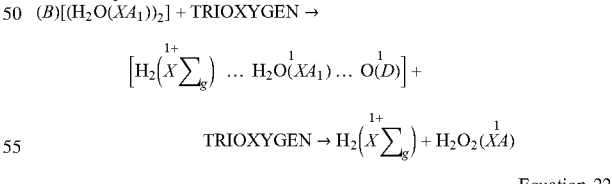 Equation 21

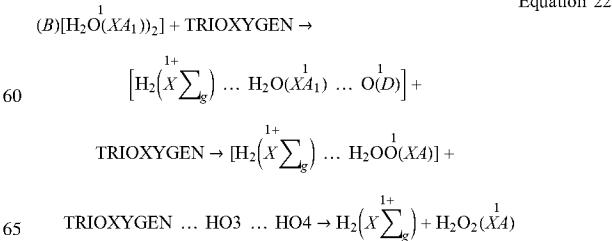 Equation 22

As can be seen above from the equations, the water solution still stores highly reactive radicals such as RNS, EMODs, hydroxyl radicals, hydroperoxyls, and the like. Hydroxyl radicals can diffuse and once they encounter a second hydroxyl radical, they can recombine to form hydrogen peroxide. As described herein, it may be understood that upon a decomposition of the water molecules, the oxygen atoms are formed in the first excited state. When the photon/phonon exposure stops and the trioxygen is depleted, the production of excited atoms ceases, too. This reinforces the fact that, without removing the wavelengths that dissociate trioxygen from the photon/phonon emissions, this reaction cannot fully proceed as described. The reactivity of ground state atoms with water is different compared to the dynamics of the trioxygen excited counterparts generated during exposure to trioxygen described in the embodiments via stated equations. The data and related discussion on the formation of the hydrogen peroxide molecule also help to explain the synthesis of atomic and molecular hydrogen during the trioxygen exposure of the oxidizing agent and/or water or solution or combination of solution composition. Here, the equations indicate that molecular hydrogen can be formed in a one-step mechanism via trioxygen decomposition of the water molecule driven by the trioxygen dose applied to the solution. Alternatively, the hydrogen atoms formed can recombine to form molecular hydrogen. The detection of hydrogen atoms during the trioxygen exposure of the oxidizing agent or water or solution or combination of solution composition phase is a direct proof that the reactions take place. Likewise, the observation of oxygen atoms during the trioxygen exposure suggests that the reactions are also an important pathway of oxygen production. The matrix may store hydrogen as hydronium or other isotopes of hydrogen and as suspended "bubbles" of hydrogen even when the photon/phonon exposure is terminated and trioxygen has ceased to be produced. By placing the matrix in a sealed container so that the suspended gases are not allowed to escape, pressure that builds up maintains the reactivity and this potential can be stored for future use. Measurements of the hydrogen gas given off by the methods have been recorded at 1.86 ppm.

Hydroxyl radicals (OH) are formed via a decomposition of a water molecule upon exposure to trioxygen. This trioxygen driven, self-sustaining circuit of reactions, generates hydrogen, oxygen, free radicals as well as oxidizing molecules including however, but not limited to, electronically modified oxygen derivatives from water or solutions containing oxidizing agents that are exposed to photon emissions which when introduced to an effective amount of a composition including water and/or an oxidizing agent compound or other compounds or solutions then exposing the composition to trioxygen, where the composition including the water and/or oxidizing agent compound, solution or both, functions together with trioxygen to lead to a reaction producing hydrogen and/or its isotopes, and/or oxygen and/or its isotopes and/or electronically modifies oxygen derivatives and or solutions derived or indirectly derived resulting from the exposure of the photon and or phonon emission wavelength(s) in the self-sustaining circuit of reactions and the resultant trioxygen used in the self-sustained circuit of reactions or the synergy therein. Also, it can be shown that there is a decomposition of the HO2 radical to molecular oxygen plus atomic hydrogen. Finally, to generate the HO2 radical, another reaction is hydrogen atoms reacting with molecular oxygen but with the application of the correct wavelengths of photon and or phonon emissions to the oxidizing agent undergoing this reaction in the self-sustained circuit of reactions, the excited state of produced hydrogen atoms and the produced molecular oxygen and the generation of trioxygen can be retarded or stopped by the discontinuance of the photon/phonon emissions used. The excited state can be preserved by sealing the reactants so that produced gases are maintained, and this allows for the reactive potential to be stored.

Thus, these embodiments uncover a significant reaction sequence that has not been previously known, appreciated or understood. By exposing an oxidizing agent to certain doses of photon and or phonon emissions, hydrogen is liberated from the reaction. Hydroperoxyls are produced and trioxygen is produced when wavelengths of photon/phonon emission that dissociate trioxygen are eliminated or reduced in intensity. This reaction generates hydrogen, oxygen, trioxygen and other free radicals as well as oxidizing molecules including but not limited to electronically modified oxygen derivatives from oxidizing agents or solutions containing oxidizing agents that are exposed to certain wavelengths of photon emissions which when introducing an effective amount of a composition including an oxidizing agent compound or other compounds or solutions then exposing the composition to photon/phonon emissions of certain wavelengths while excluding the wavelengths from photon/phonon emissions that would disallow the formation of trioxygen, where the composition including the oxidizing agent compound, solution or both, functions together with the photon/phonon emissions of certain wavelength or wavelengths to lead to a reaction producing trioxygen, hydrogen and/or its isotopes, and/or oxygen and/or its isotopes and/or electronically modifies oxygen derivatives and or solutions derived or indirectly derived resulting from the exposure to photons/phonons of said wavelength(s) or the synergy therein. The oxidizing potential of trioxygen is slightly less than the oxidizing potential of hydroxyl radicals, but it is greater than the oxidizing potential of hydrogen peroxide. While the commonly accepted lifetime of hydroxyl radicals is a few nanoseconds, trioxygen has been shown to maintain its reactivity for hours. The ability of trioxygen to linger for an extended period allows for a "stored" oxidizing effect. The "stored" oxidizing effect can be tapped to provide reactive oxygen species as needed and the "stored" oxidizing effect feeds the self-sustaining circuit of reactions so that reactive oxygen species are generated until one of the reactants is depleted. FIG. 2 reflects testing that displays this "stored" effect. When comparing the oxidizing agent control versus the photon/phonon enhanced oxidizing agent solution, there is over a 5-log increase in efficacy with the photon/phonon enhanced oxidizing agent solution. By employing the self-sustaining circuit of reactions, we have increased the efficacy and reserved the use of the electronically modified oxygen derivatives that are being continuously generated so that they are available for use over an extended period of time as evidenced in the "week 4" table above.

The equations are exemplary and are non-limiting with respect to wavelengths, time of exposure to photon/phonon emissions, intensity of photon/phonon emissions or total dose of photon/phonon emissions. By exposing the oxidizing agent or agents to photon/phonon emissions from 100 nm to 1200 nm, where the photon/phonon emission of wavelengths that dissociate trioxygen are excluded, a synergistic reaction occurs creating trioxygen and other electronically modified oxygen derivatives and disrupting the typical disassociation reaction of the oxidizing agent or agents. Chemicals such as oxidizing agents exist in a state of flux whereby, they disassociate and reassociate as self-ionization reactions occur.

When alterations of the expected disassociation reactions occur, new compounds or variations in compound concentrations occur. These new compounds or variations in compound concentrations created in the photon/phonon emission generated synergistic reaction enable a known oxidizing agent to create reactions that have not been observed or reported previously. By restricting the photon/phonon emissions applied to the oxidizing agent so that dissociation of trioxygen is reduced or eliminated, a reaction is produced that has previously not been appreciated or reported. This is shown by the photon/phonon emissions typically produced as having wavelengths that dissociate trioxygen when said photon/phonon emission is applied to oxidizing agents. Restricting the dissociation of trioxygen has produced reaction products that have not been described for this reaction previously or that have not been produced in quantities that are shown in the embodiments.

The reactants may contain enzymes, stabilizers or other substances that affect the overall reaction rate. Enzymes, stabilizers and/or other substances can be destroyed or inactivated by temperature variations, pH shifts and other means. These techniques may be employed to arrive at the most favorable reaction outcomes. It is understood that phosphoric acid (H3PO4) is generally added to commercially available oxidizing agent solutions such as hydrogen peroxide as a stabilizer to inhibit the decomposition of the oxidizing agent. Several types of reagents, such as H3PO3, uric acid, Na2CO3, KHCO3, barbituric acid, hippuric acid, urea, and acetanilide, have also been reported to serve as stabilizers for oxidizing agents such as hydrogen peroxide. These stabilizers have been shown to have a catalyst effect on some of the described reactions and an inhibitory effect on other areas of the reactions, but the reaction may proceed with or without stabilizers present in oxidizing agents, as desired.

The embodiments describe methods and techniques where, by altering the typical disassociation wavelength of photon/phonon emission applied to oxidizing agents, the ensuing reaction generates previously unrecorded reaction byproducts and/or quantities of byproducts.

The embodiments further demonstrate the discovery of altering the expected reactions found by the disassociation of trioxygen while photon/phonon emissions of certain wavelengths is targeted to oxidizing agents and by so altering the expected disassociation compounds that are generated and that have not been reported from the typical disassociation reactions. This discovery has applications in many industries. By increasing the efficacy of oxidizing agents, common chemical reactions involving oxidizing agents may be accomplished using less volume and/or a lower concentration of oxidizing agents. Oxidizing agents can be used to precipitate material out of solution. Increasing the efficacy of the oxidizing agent allows for this precipitation with less oxidizing agent. Oxidizing agents have antimicrobial properties. By increasing the antimicrobial efficacy with the methods described herein, concentrations of oxidizing agents utilized can be reduced while efficacy can be maintained or increased. By utilizing this principle in a small micron antimicrobial dry fog photon/phonon enhanced oxidizing solution, an extremely low concentration of a photon/phonon enhanced hydrogen peroxide solution (with wavelengths that dissociate trioxygen excluded) can be deposited in ambient air through a HVAC system rendering the air almost microbe free in a matter of hours.

By increasing the availability of ROS in the photon emission enhanced oxidizing agent solution, current applications of oxidizing agents in the semiconductor industry, paper industry, petrochemical industry and other commercial applications can be accomplished faster and/or more economically and/or more environmentally responsibly. The uses of the methods described herein are too numerous to list but are widespread in diverse industries from oil and gas to health care and beyond.

The foregoing description and accompanying figures illustrate the principles, preferred embodiments, and modes of operation of the invention. However, the invention should not be construed as being limited to the embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A method for generating enhanced effectiveness displayed over extended time products from photo-oxidation reactions, photocatalytic reactions and/or photochemical combined with photocatalytic reactions which include one or more of reactive nitrogen species, hydrogen and its isotopes, oxygen and its isotopes, and electronically modified oxygen derivatives, reactive oxygen species, trioxygen, and free radicals, comprising:

applying at least one oxidizing agent to a target where a synergistic reaction is to take place wherein the at least one oxidizing agent is selected from the group consisting of oxygen ($O_2$), trioxygen ($O_3$), hydrogen (H), hydrogen peroxide ($H_2O_2$), inorganic peroxides, Fenton's reagent, fluorine ($F_2$), chlorine ($Cl_2$), halogens, nitric acid ($HNO_3$), nitrate compounds, sulfuric acid ($H_2SO_4$), peroxydisulfuric acid ($H_2S_2O_8$) peroxymonosulfuric acid ($H_2SO_5$), sulfur compounds, hypochlorite, chlorite, chlorate, perchlorate, other analogous halogen compounds, chromic acid, dichromic acid, calcium oxide, chromium trioxide, pyridinium chlorochromate (PCC), chromate, dichromate compounds, hexavalent chromium compounds, potassium permanganate ($KMnO_4$), sodium perborate, permanganate compounds, nitrous oxide ($N_2O$), nitrogen dioxide/dinitrogen tetroxide ($NO_2/N_2O_4$), urea, potassium nitrate ($KNO_3$), sodium bismuthate ($NaBiO_3$), ceric ammonium nitrate, ceric sulfate, cerium (IV) compounds, peracetic acid, and lead dioxide ($PbO_2$);

applying photon or phonon emissions in a wavelength range of 100 nm to 1200 nm to the oxidizing agent and/or the target;

forming a synergistic reaction and producing at least one of photo-oxidation products, photocatalytic products, and a photochemical combined with photocatalytic products by photo/phonon absorption of the oxidizing agent and/or oxidizing agent and target to be treated; and generating at least trioxygen, hydrogen, oxygen, and hydroxyl radical by combining the photo-oxidation products, photocatalytic products, and/or photochemical combined with photocatalytic products.

2. The method of claim 1, wherein further comprising limiting or excluding wavelengths selected from the group consisting of: 197 nm-198 nm, 263 nm-264 nm, 307 nm 308 nm, 402 nm-403 nm, 452 nm-453 nm, 599 nm-600 nm, and 1118 nm-1119 nm.

3. The method of claim 1, wherein the photon emissions are applied by an emission source selected from the group consisting of an electromagnetic radiation emitting bulb, Light Emitting Diode, x-ray generator, and laser.

4. The method of claim 1, wherein an oxidizing agent dispenser is used applying the at least one oxidizing agent to the target where the described reaction is to take place, and the oxidizing agent dispenser comprises at least one of a pump, mister, fogger, atomizer, diffuser, or electrostatic sprayer.

5. The method of claim 1, further comprising applying additional reactants at various stages to aid the oxidizing reaction, wherein the additional reactants are selected from the group consisting of enzymes, catalysts, stabilizers, and flocculants.

6. The method of claim 1, further comprising generating an augmented oxidizing agent (AOA) by the photon emission exposure of at least one oxidizing agent and to precipitating and/or agglomerating material out of a liquid, plasma, air or gas.

7. The method of claim 1, wherein the photon enhanced oxidizing agent is an antimicrobial agent.

8. The method of claim 1, wherein the photon enhanced oxidizing agent is a bleaching agent.

9. The method of claim 1, wherein the photon and or phonon emission exposure is a single wavelength or multiple wavelengths, applied either independently or simultaneously, continuously or pulsed.

10. The method of claim 1, wherein the photon emissions are applied as a single wavelength or multiple wavelengths, applied either independently or simultaneously, and either continuously or pulsed.

11. The method of claim 1, wherein the photon emissions are applied to the oxidizing agent, the target, and/or the substance to be treated at a dose that is varied or not varied.

12. The method of claim 1, wherein the amount of the at least one oxidizing agent is in a range from 1 part per million to 50 percent of the volume of the target and/or substance to be treated.

13. The method of claim 1, wherein the photon emission is applied to the at least one oxidizing agent before the at least one oxidizing agent is applied to the target and/or the substance to be treated, the target and/or the substance to be treated furthers the oxidization reaction or produces one or more additional reaction, and the further or one or more additional reactions are not dependent on continued or additional application of the photon and/or phonon emissions.

14. The method of claim 1, wherein the photon emission is applied to the at least one oxidizing agent after the at least one oxidizing agent is applied to the target and/or substance to be treated so that trioxygen and other reaction products are generated after the at least one oxidizing agent is applied to the target and/or substance to be treated, and the oxidization reaction is readied but not initiated until a preset time or event.

15. The method of claim 1, wherein the oxidation reaction utilizing the photon enhanced oxidizing agent occurs in a sealed container whereby gases created by the oxidation reaction are not allowed to escape.

16. The method of claim 1, wherein the at least one oxidizing agent is selected from the group consisting of oxygen ($O_2$), trioxygen ($O_3$), hydrogen (H), hydrogen peroxide ($H_2O_2$), inorganic peroxides, Fenton's reagent, fluorine ($F_2$), chlorine ($Cl_2$), halogens, nitric acid ($HNO_3$), nitrate compounds, sulfuric acid ($H_2SO_4$), peroxydisulfuric acid ($H_2S_2O_8$) peroxymonosulfuric acid ($H_2SO_5$), sulfur compounds, hypochlorite, chlorite, chlorate, perchlorate, other analogous halogen compounds.

17. The method of claim 1, further comprising determining the formulation of the at least one oxidizing agent, wherein the formulation is based on one or more properties of whether the target and/or substance to be treated is under aerobic or anaerobic conditions, pH of the target and/or substance to be treated, temperature of the target and/or substance to be treated, salinity of the target and/or substance to be treated, consortium or population characteristics of organisms or micro-organism present, content of the target and/or substance to be treated, or content of any biofilms associated with the target and/or substance to be treated.

18. The method of claim 1, wherein the at least one photon enhanced oxidizing agent further comprises at least one other substance that aids in a desired process when applied to the target and/or substance to be treated, the desired process selected from the group consisting of antimicrobial properties, anti-corrosion properties, anti-neoplastic properties, thermal properties, explosive properties, precipitation properties, electrochemical properties, and power generation properties.

19. The method of claim 1, wherein at least one of the photon emission wavelengths, intensity, duration, or location relative to the target and/or substance to be treated is determined on the basis of any one or more of: the density and light absorbing or reflection quality of the target and/or substance to be treated; the size, shape, or composition of a container containing the target and/or substance to be treated; conditions or properties of the environment of the target and/or substance to be treated; whether the target and/or substance to be treated is under aerobic or anaerobic conditions; pH, temperature, salinity of the target and/or substance to be treated; consortium or population characteristics of any organisms or microorganisms present in the target and/or substance to be treated; microbial content of the target and/or substance to be treated; and microbial content of any biofilm present in the target and/or substance to be treated; or a container containing the target and/or substance to be treated.

* * * * *